(12) United States Patent
Gavriely et al.

(10) Patent No.: US 8,241,223 B2
(45) Date of Patent: Aug. 14, 2012

(54) COUGH DETECTOR (75) Inventors: Oren Gavriely, Haifa (IL); Noam Gavriely, Haifa (IL)

(73) Assignee: Isonea Limited, Armadale, Victoria (AU)

( * ) Notice: Subject to any disclaimer, the term of this patent is extended or adjusted under 35 U.S.C. 154(b) by 481 days.

(21) Appl. No.: 11/912,897

(22) PCT Filed: Apr. 30, 2006

(86) PCT No.: PCT/IL2006/000517
§ 371 (c)(1),
(2), (4) Date: May 18, 2008

(87) PCT Pub. No.: WO2006/117780
PCT Pub. Date: Nov. 9, 2006

(65) Prior Publication Data
US 2009/0216127 A1 Aug. 27, 2009

(51) Int. Cl.
*A61B 5/08* (2006.01)
*A61B 5/00* (2006.01)
*A61B 8/00* (2006.01)

(52) U.S. Cl. ........ 600/532; 600/586; 600/453; 600/538; 327/40; 327/44; 327/47

(58) Field of Classification Search .................. 600/532, 600/463, 428, 453; 128/204.23
See application file for complete search history.

(56) References Cited

U.S. PATENT DOCUMENTS

| | | | |
|---|---|---|---|
| 4,094,304 A | 6/1978 | Wright | |
| 4,173,897 A | 11/1979 | Forstermann et al. | |
| 4,197,856 A | 4/1980 | Northrop | |
| 4,240,281 A | 12/1980 | Lather et al. | |
| 4,326,416 A | 4/1982 | Fredberg | |
| 4,653,327 A | 3/1987 | Varterasian et al. | |
| 4,671,295 A * | 6/1987 | Abrams et al. | 600/463 |
| 4,982,738 A | 1/1991 | Griebel | |
| 5,010,889 A | 4/1991 | Bredesen et al. | |
| 5,165,417 A | 11/1992 | Murphy, Jr. | |
| 5,218,969 A | 6/1993 | Bredesen et al. | |
| 5,331,967 A | 7/1994 | Akerson | |
| 5,560,351 A | 10/1996 | Gravenstein et al. | |

(Continued)

FOREIGN PATENT DOCUMENTS

GB 2240392 A 7/1991
(Continued)

OTHER PUBLICATIONS

T. Rosqvist, et al. "Tool Kit for Lung Sound Analysis" Medical and Biological Engineering & Computing, vol. 33, No. 2 Mar. 1995, pp. 190-195.

(Continued)

*Primary Examiner* — Long V Le
*Assistant Examiner* — Farshad Negarestan
(74) *Attorney, Agent, or Firm* — Greenberg Traurig LLP; Cecily Anne O'Regan (57) ABSTRACT

A device for detecting and counting coughing events is provided. In one embodiment a sensor for sensing and transducing low frequency and high frequency mechanical vibrations, sends signals to a coincidence detector that determines if high and low signals coincide. In another embodiment, ultrasonic energy is introduced to the trachea and if Doppler shift in frequency is detected, association is made to a coughing event. In another embodiment a change in the impedance of the neck is considered associated with coughing event if correlated over time with a specific mechanical frequency sensed.

9 Claims, 6 Drawing Sheets

U.S. PATENT DOCUMENTS

| | | | |
|---|---|---|---|
| 5,562,608 A | 10/1996 | Sekins et al. | |
| 5,588,439 A | 12/1996 | Hollub | |
| 5,591,130 A | 1/1997 | Denton | |
| 5,844,997 A | 12/1998 | Murphy, Jr. | |
| 5,893,361 A | 4/1999 | Hughes | |
| 6,058,932 A | 5/2000 | Hughes | |
| 6,116,241 A | 9/2000 | Huygen et al. | |
| 6,139,505 A | 10/2000 | Murphy | |
| 6,168,568 B1 | 1/2001 | Gavriely | |
| 6,241,683 B1 | 6/2001 | Macklem et al. | |
| 6,261,238 B1 * | 7/2001 | Gavriely | 600/532 |
| 6,364,849 B1 | 4/2002 | Wilcox | |
| 6,383,142 B1 | 5/2002 | Gavriely | |
| 6,428,483 B1 | 8/2002 | Carlebach | |
| 6,942,626 B2 | 9/2005 | Salisbury et al. | |
| 7,479,115 B2 | 1/2009 | Savic | |
| 2005/0011279 A1 * | 1/2005 | Takeda et al. | 73/861.26 |
| 2005/0154307 A1 * | 7/2005 | Hirayama et al. | 600/453 |
| 2005/0187464 A1 * | 8/2005 | Ho et al. | 600/428 |
| 2006/0243280 A1 | 11/2006 | Caro | |
| 2007/0055175 A1 | 3/2007 | Caro | |
| 2008/0283062 A1 * | 11/2008 | Esposito, Jr. | 128/204.23 |
| 2009/0171231 A1 | 7/2009 | Caro et al. | |
| 2009/0216127 A1 | 8/2009 | Gavriely | |
| 2011/0230777 A1 | 9/2011 | Fu | |

FOREIGN PATENT DOCUMENTS

| | | |
|---|---|---|
| WO | WO91/03981 A1 | 4/1991 |
| WO | WO96/19142 A1 | 6/1996 |
| WO | WO97/29687 A1 | 8/1997 |
| WO | WO2004/091503 A2 | 10/2004 |

OTHER PUBLICATIONS

A. Cohen, et al.: "Analysis and Automatic Classification of Breath Sounds" IEEE Transactions on Biolmedical Engineering, vol. 31, No. 9, Sep. 1984, NY, USA pp. 585-590.

A. Cohen: "Signal Processing Methods for Upper Airway and Ppulmonary Dysfuncation Diagnosis", IEEE Engineering in Medicine & biology, vol. 9, No. 1, Mar. 1990, NY USA, pp. 72-75.

Wodicka et al.; "Bilateral Asymmetry of Respiratory Acoustic Transmission;" Sep. 1994; Medical & Biological Engineering & Computing; vol. 32, pp. 489-494; XP000469338.

* cited by examiner

COUGH DETECTOR

FIELD OF THE INVENTION

This invention relates to detection of signals from the body of a person or an animal and more specifically to the detection of cough.

BACKGROUND OF THE INVENTION

Physiology

Cough is a physiological reflex that helps clear secretions and foreign elements from the airways. The cough reflex is triggered by stimulation of mechano-receptors in the larynx, trachea, main carina and central airways. The afferent sensory signals are transmitted via pharyngeal branches of the glossopharyngeal nerve and by sensory fibers of the vagus nerve to the medulla oblongata. The signals are processed and a motor sequence of muscle activation is generated to create the cough.

Each cough starts with an inspiration, followed by closure of the glottis while the expiratory muscles (rectus abdominis and the intercostals muscles) contract. This contraction against a closed glottis rapidly elevates the intra-thoracic pressure. The glottis then opens and a burst of exhaled air flows through the trachea and out the mouth. The balance of forces on the tracheal wall, which includes the Bernoulli Effect, creates a net negative transmural pressure and dynamic tracheal collapse. As the trachea gets narrower, the speed of the air molecules through it increases, which further increases the negative transmural pressure and promotes additional collapse. The speed of air in the trachea during a cough may reach 100 m/s. The rapid gas movement along the tracheal walls creates substantial sheer forces, which help dislodge particles and secretions from the wall and into the air stream. These elements are then swept away with the gas outside of the airways through the glottis.

Each cough may have one or more components, or bursts for a single inspiration. Each burst is terminated by one of the following three mechanisms: (a) re-closure of the glottis, (b) termination of the expiratory muscles activity, or (c) exhaustion of the available gas flow reserve in the lung.

Patho-Physiology

While the cough reflex is an important component of the lung defense mechanisms, it is often a source of annoyance and concern to the patient. Chronic cough (i.e., frequent coughing that lasts for 2 weeks or more) may be an important sign of a lung disease (e.g., asthma, chronic bronchitis, malignancy, bronchiectasis, lung fibrosis or TB). There are, however, many cases where persistent cough is self-perpetuating, so that each cough spell applies such forces to the airway mucosa that stimulates and triggers a subsequent paroxysm, even in the absence of secretions or foreign bodies in the airways ("dry cough").

Epidemiology

The prevalence of cough is high, leading to more visits to Drs' offices than any other single clinical symptom or sign. It is estimated that as many as 3% of all office visits to primary care physicians in the US are due to cough. Consequently, the market for cough remedies is huge, extending from various natural herbs and aromatic syrups to narcotic habit-forming drugs (e.g. codeine). The total market of antitussive medications in the US alone is estimated in Billions of $US.

Cough Detection

With cough being such a common problem, the need for methods and devices for objective detection and quantification of cough is obvious. Cough detection is needed in order to assess the severity of cough in an individual patient, to determine the association between coughing and certain offending conditions, such as occupational exposure, and for the evaluation and validation of the effectiveness of new and old cough remedies.

There have been several methods for detection of cough and for the creation of a log of coughing activity in a person or an animal. The simplest and, to this time, the most accurate method of detecting cough is by one or more trained observers who are either present in person with the index patient, or are listening and observing a video tape recording of the patient. As such, this method is often used as a reference ("gold standard") for validation of an automated cough detection device.

Automated cough detection has been attempted and the following is a brief description of the available prior art. These methods may be divided into those that use the cough sound alone and those that use the cough sound in combination with other signals. Cough detection by loud-sound detection and recording on a sound-activated tape (or digital) recorder have been used in research by Mori et Al. (1987) and Sestini at Al (1991). The timing of the tape activation may also be recorded with each loud sound. The total recording time, or the number of recorder activations are used as a cough activity index. This method is sensitive, but lacks specificity since other loud noises in the environment may trigger the recording as well. Subsequent auditory screening of the recorded sounds by a trained observer, or an automated algorithm (see below) may improve the specificity of this method.

Earis and co-workers (1994, 2002, 2003) described digital signal processing methods including spectral analysis and voice analysis methods to evaluate loud sounds to differentiate between cough sounds and other sounds such as vocalization. These studies as well as studies by other researchers analyzed ambient sounds recorded with a single microphone.

Other methods to detect coughs use two or more signals. Bush et Al., described a method by which a microphone output is used in combination with the signals from Electromyograph (EMG) electrodes placed on the abdominal muscles. These muscles contract in order to generate the elevated expiratory intra-thoracic pressure needed for an effective cough. Salmi et Al (Chest, 1988) used a static charge-sensitive bed to detect the cough-induced fast movements of the body and an ambient microphone output. Gavriely N. described in U.S. Pat. Nos. 6,261,238 and 6,168,568 a method in which the loud output of a microphone alongside a simultaneous sudden motion of the chest detected by a chest motion detector such as an electrical impedance plethysmograph are used as the first phase of cough detection algorithm.

DETAILED DESCRIPTION OF THE PRESENT INVENTION

Figure 1:
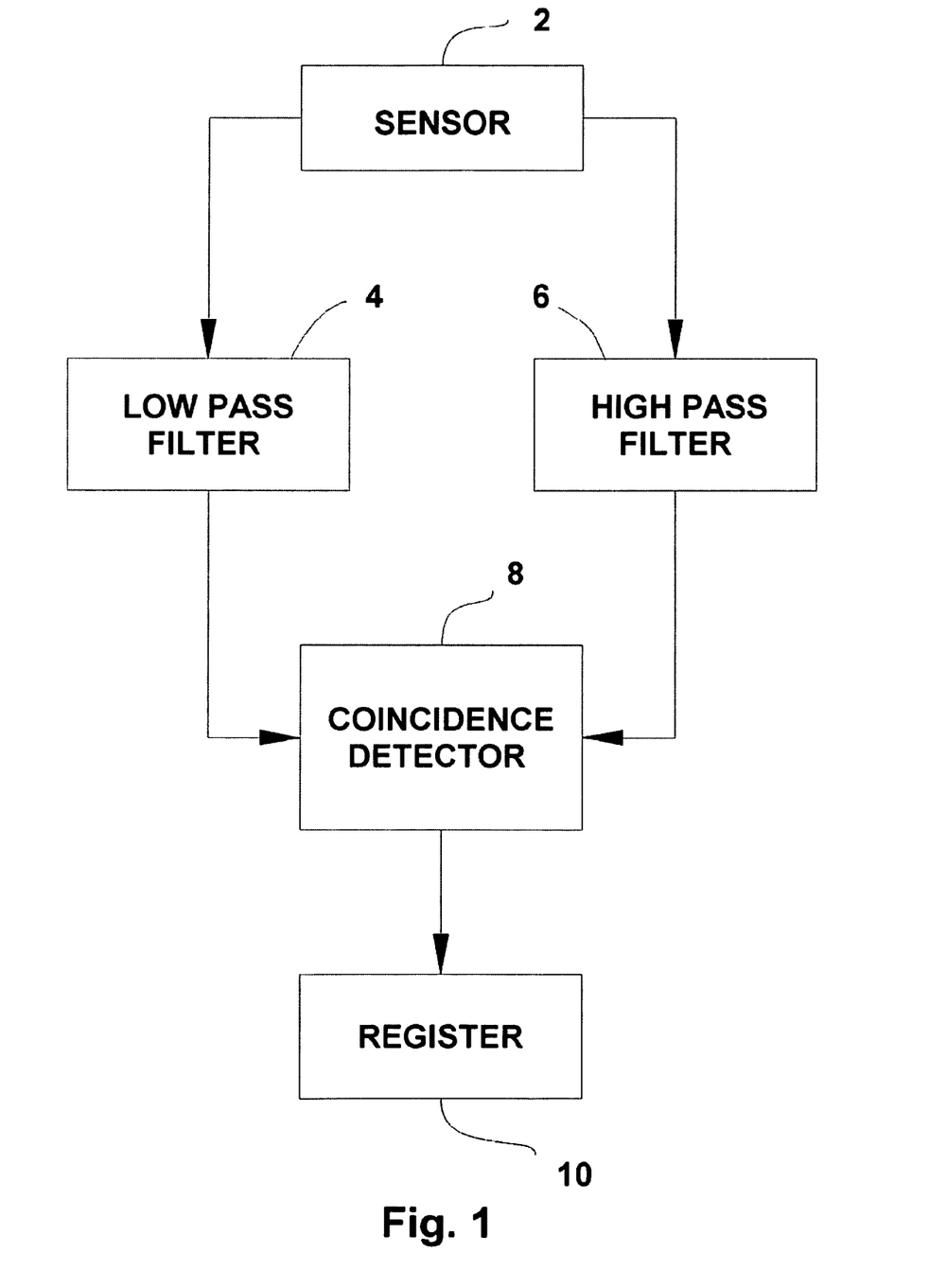
FIG. 1 is block diagram description of the structural aspects of a cough detector of the invention.
Figure 6A:
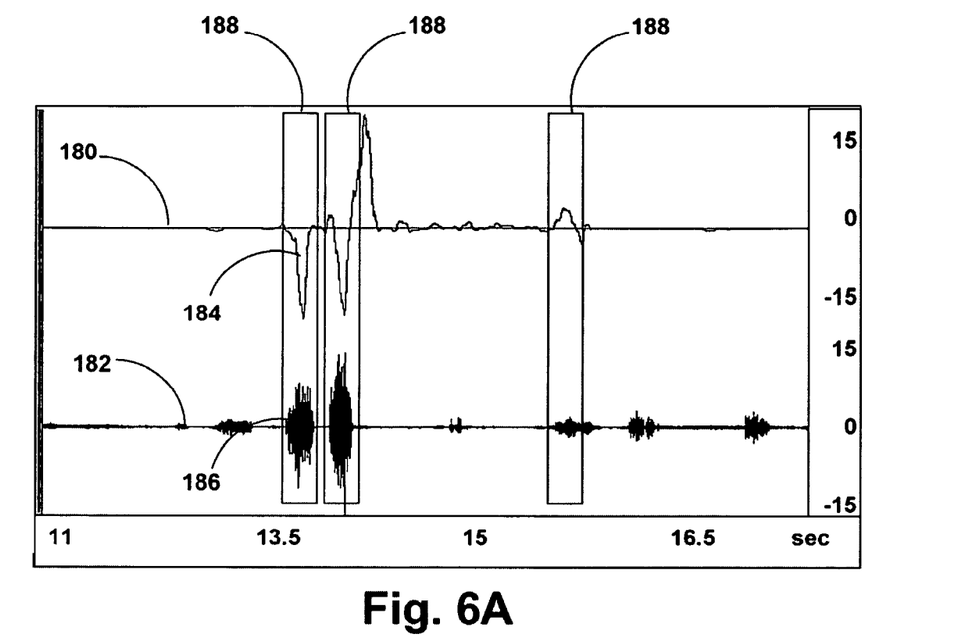
FIG. 6A is a graphic depiction of the low and high frequency components of the deformation cough detector sensor output during coughs.
Figure 6B:
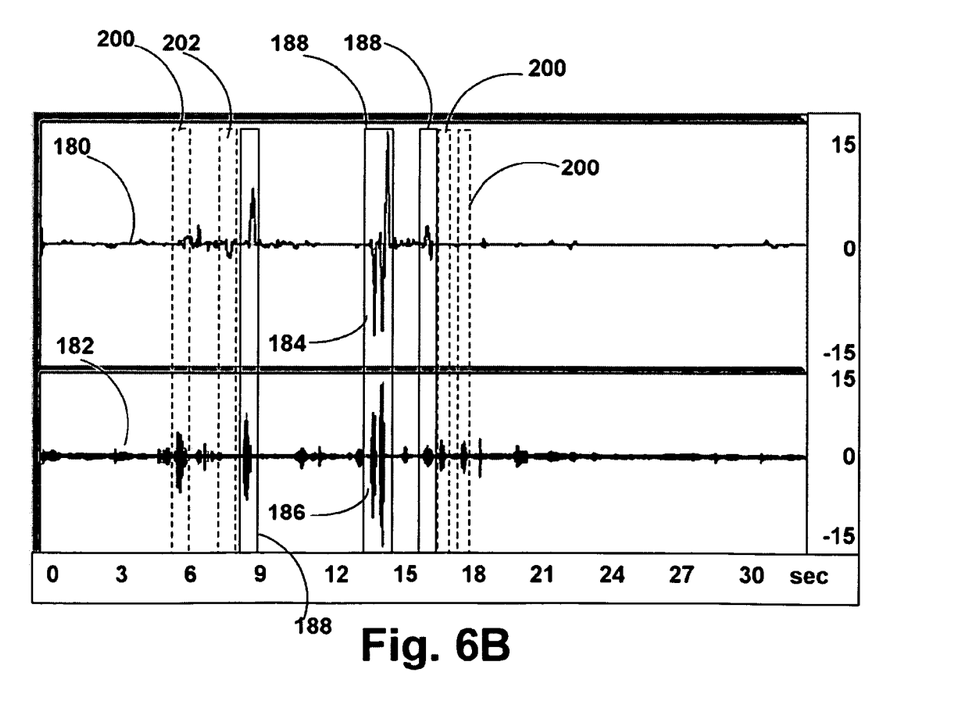
FIG. 6B is a graphic depiction of the low and high frequency components of the deformation cough detector during cough and during non cough activities.

In accordance with the present invention, a cough detector is provided that identifies coughs and draws a distinction between coughing sounds and other loud noises. It also differentiates between cough-induced rapid movement of tracheal air and other rapid movements. A sensor placed over the trachea at the anterior cervical area is used to collect the sound signals. The sensor collects the signal and transduces it into an electric signal. Any sensor known in the art able to detect simultaneously, both the high frequency acoustic signal of cough and the low frequency mechanical signal generated by the rapid flow of air and tracheal deformation during cough is applicable. The detection of the two frequencies may be achieved using a single sensing element in which case the sensor is simple, or alternatively by two separate sensing elements packaged together, in which case the sensor is compound. An example of a system embodying the invention is described schematically in FIG. 1 to which reference is now made. The electrical output of the sensor 2 is channeled to two separate frequency filters 4 and 6. Low pass filter 4 selectively passes signals associated with events that correspond to the rapid expiratory flow of air in the trachea or the sudden change in the tracheal dimensions associated with its dynamic collapse during cough. Such events typically generate vibrations in the frequency range of 0.5 to 10 Hz. High pass filter 6 selectively passes signal associated with brief loud sounds in the frequency range of 200 to 2000 Hz. The amplitude threshold is typically 70 dB absolute sound level pressure or higher and the duration threshold is typically between 0.15 to 1.5 sec or narrower. Coincidence detector 8 receives signals from both filters. In the event that signals from both filters arrive simultaneously, coincidence detector identifies the event as a a coughing event. This data is then transmitted to a data register 10 that keeps log of the coughing activity detected by sensor 2. Examples of coughs where both thresholds are violated at the same time are shown in FIG. 6A and of acoustic and mechanical events that did and did not coincide are shown in FIG. 6B.

Figure 2A:
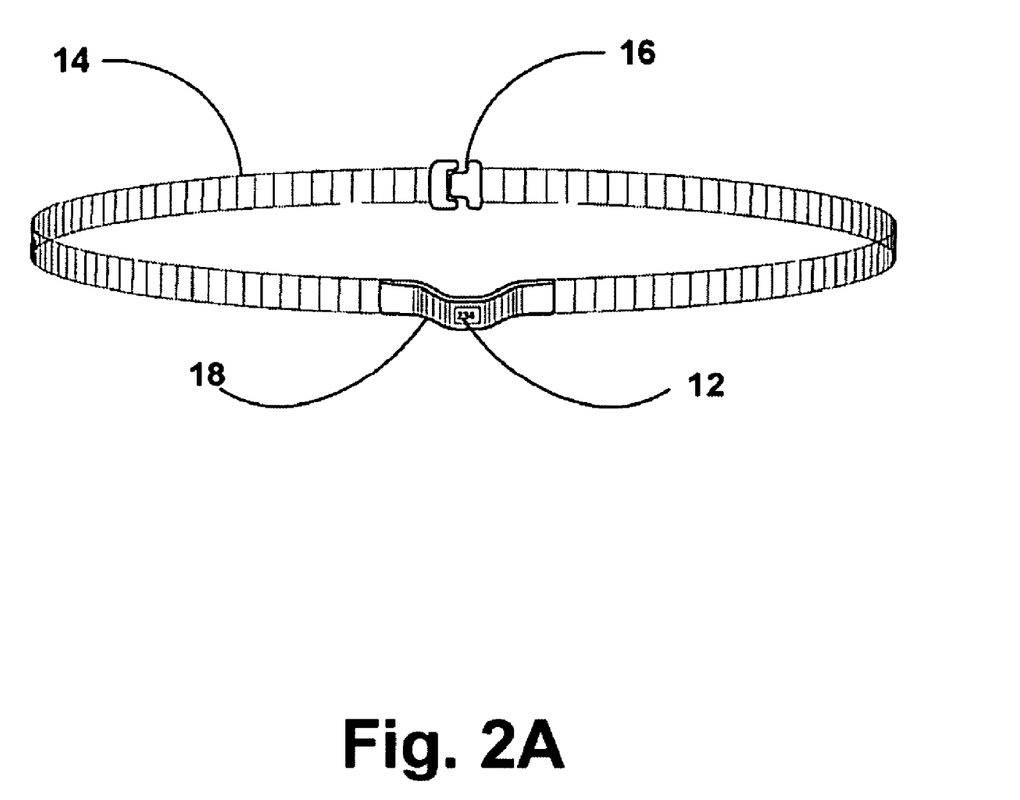
FIG. 2A is a schematic isometric description of the cough detector.
Figure 2B:
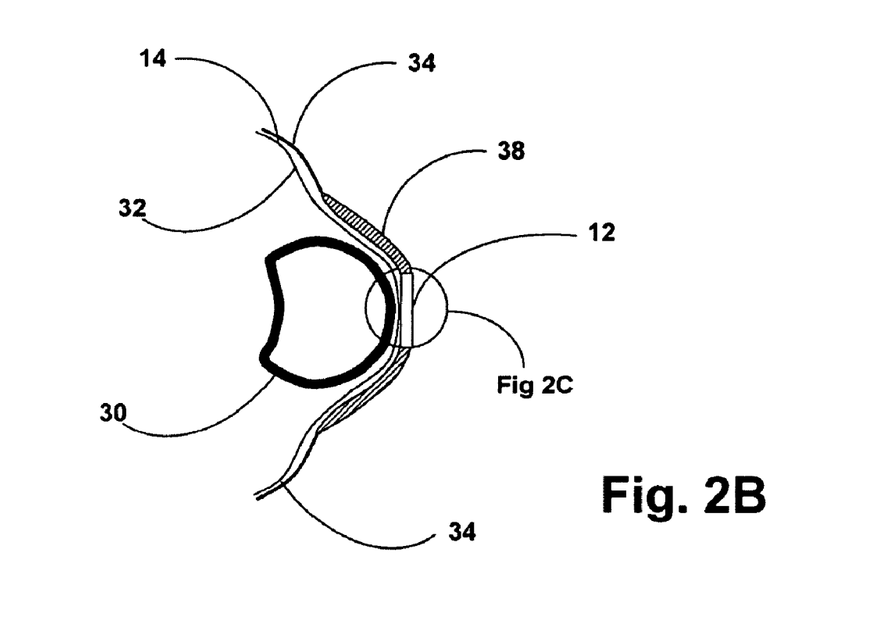
FIG. 2B is a transverse section through the frontal active element of the deformation cough detector.
Figure 2C:
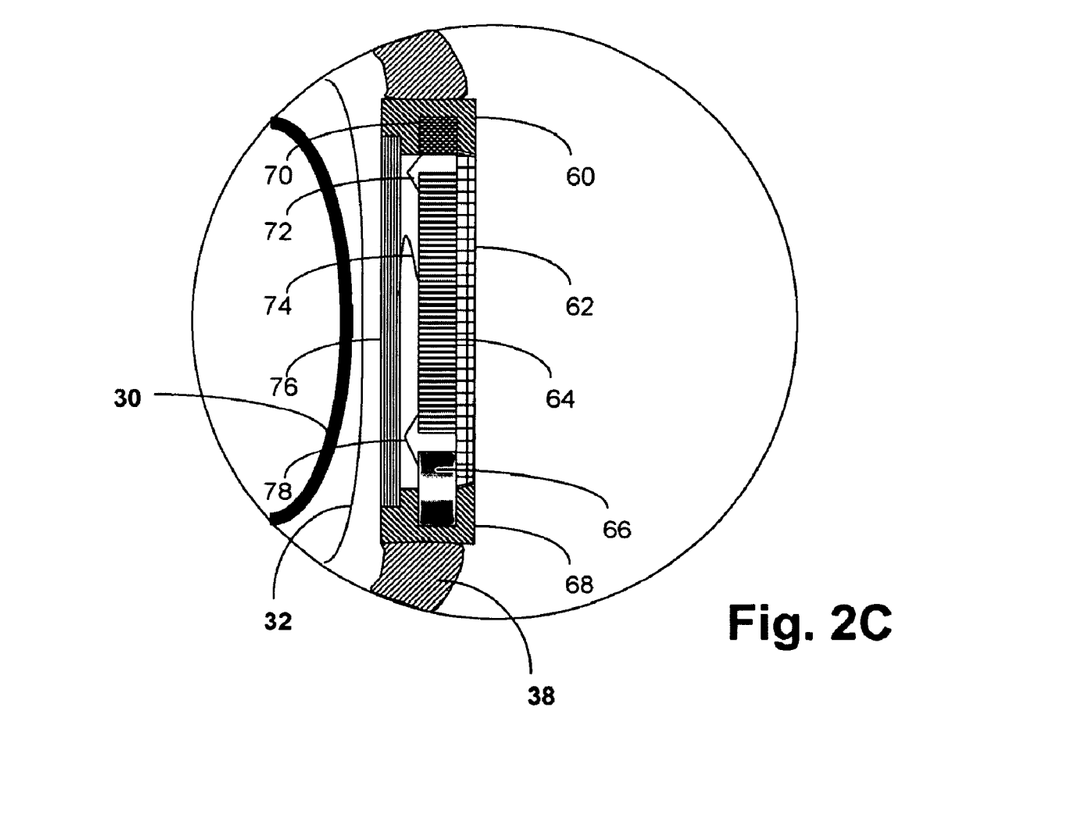
FIG. 2C is an enlarged transverse section through the active detection element of the deformation cough detector

A cough detector in accordance with the present invention has a sensor that is donned on the neck and is self-enclosed with all the electronic elements necessary for the thresholds detection and data logging. In FIG. 2A to which reference is now made, a cough detector (CD) 12 hung by the circumferential band 14 around the neck so that the CD and positioned over the lower segment of the cervical trachea is shown. A latch 16 is used to adjust the length and the tension of the band 14 to fit snuggly to the neck yet without strangulating the patient. The active element 12 of the CD optionally includes a visible display of the cough activity 18, or a decorative element. In FIG. 2B to which reference is now made, an enlarged cross section of the trachea 30 is shown under the patient's skin 32. The frontal ends of the circumferential band 34 are shown connected to the housing strap of the CD 38. The active element of the CD 12 is connected on both sides to the housing strap 38 and is in close contact with the pre-tracheal skin surface 32. The main components of the active element of the CD are shown in an enlarged form in FIG. 2C to which reference is now made. Sections of the tracheal wall 30 and the overlying skin 32 are also shown. The housing of the active element 60 is shown connected to the housing strap 38. The housing 60 holds within it an optional display 62 and a processor 64 that contains the electronic and/or digital technology needed to analyze, store, retrieve, display or transmit the data. The CD active element is powered by a battery 66 that is held in a groove 68 in the housing 60. The battery is connected to the processor 64 via wires 78. The stored data may be transmitted to a remote host computer or data logger (not shown) via a wire or wireless transmitter 70 connected to the processor 64 via wires 72. The sensing element 76 of the CD active element is capable of picking up both low and high frequency mechanical oscillations when brought into contact with the skin 32 overlaying the trachea 30. A preferred embodiment of the sensing element 76 is a piezoelectric crystal mounted on a metallic membrane such as model KBS-27DA-5AS transducer, commercially available from Kyocera Corporation of Japan. The sensor 76 is shown connected to the processor 64 via wires 74.

Figure 3:
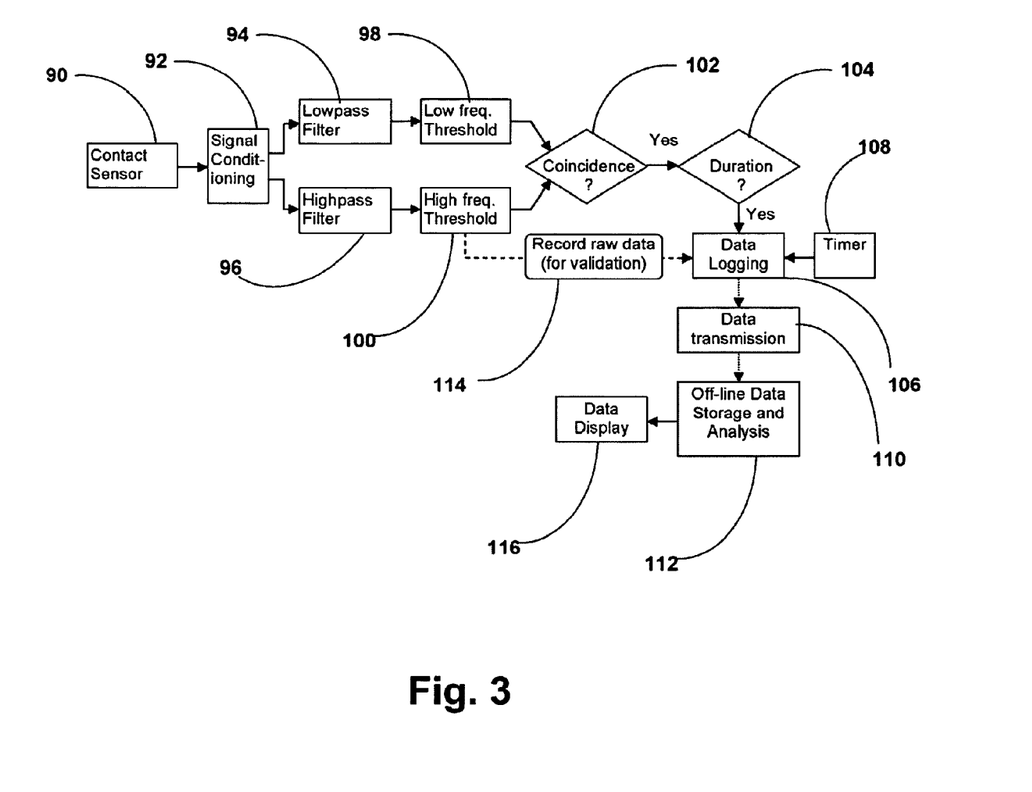
FIG. 3 is a block diagram of the detection method of the deformation cough detector.

A block diagram or a preferred embodiment of the deformation CD method is shown in FIG. 3 to which reference is now made. The signal from the contact sensor 90 is amplified in the signal conditioning element 92 and then filtered by the lowpass filter 94 and the highpass filter 96. The filtration of the signal is within low and high frequency ranges as outlined above. The low frequency signal is transmitted to a low frequency threshold detector 98 that identifies events where the low frequency signal is higher than the threshold. The threshold may be a fixed or adaptive threshold. For the duration that the low frequency threshold has been exceeded the low frequency threshold detector 98 emits a signal, which may be either analog, or digital. The high frequency signal is transmitted to a high frequency threshold detector 100 which identifies events that are of higher amplitude than the threshold. Here, too, the threshold may be fixed or adaptive. For the duration that the high frequency threshold has been exceeded the high frequency threshold detector 100 emits a signal, which may be either analog, or digital. Both signals are then transmitted to a coincidence detector 102 which determines whether the signals arriving from the low and the high frequency channels are simultaneous. If the signals are determined to be coincidental, the coincidence detector 102 generates a continuous signal for the duration of the coincidence. This signal is then transmitted to the duration detector 104, which determines whether the duration of the coincidental signal was within the range of cough durations as outlined above. If the duration of the coincidence was within the range, the duration detector 104 generates a signal that activates the data logging unit 106. The time of the event is also recorded on the data logger from a timing (clock) device 108. This event may also trigger recordation of a segment of raw data (sounds) from the time duration of 2-3 seconds that preceded the trigger event and were continuously tracked and transiently recorded by the recording element 114. This recording may be used for additional signal processing or for validation through listening by experts. The information from the data logger 106 may then be transmitted by means of a data transmission element 110 which may be via wire, or wireless and may be in a digital or an analog format. The data is transmitted to another data storage device for permanent recordation, further analysis 112, validation or for preparation for display by the data display member 116.

Figure 4:
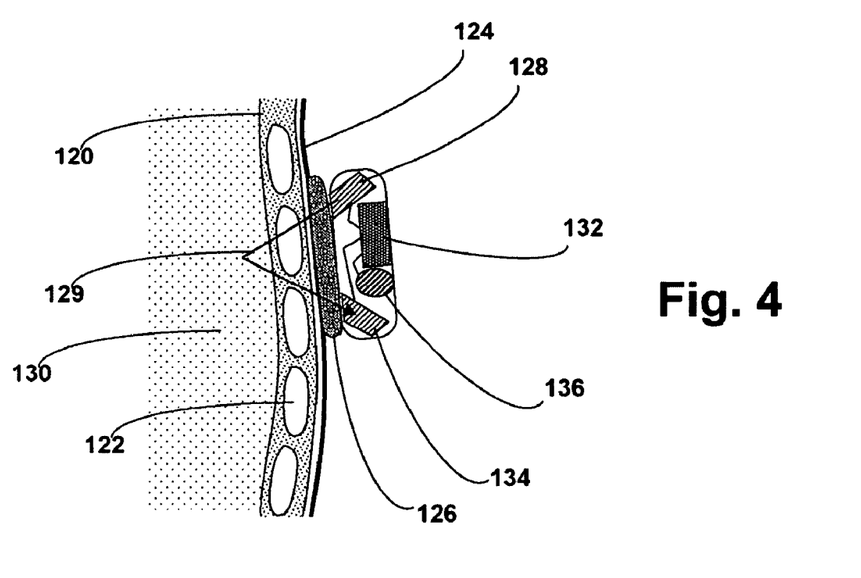
FIG. 4 is a longitudinal section through the ultrasonic cough detector

An alternative preferred embodiment of the CD is based on detection of the acute sudden expiratory tracheal flow and deformation generated by coughing through an ultrasonic flow detector shown in FIG. 4 to which reference is now made. A longitudinal sagittal section through the tracheal wall 120 and its cartilage rings 122 and overlaying skin 124 is shown. The sensing element is coupled to the neck surface by an acoustically conductive jell pad 126, which facilitates the transmission of the ultrasonic signal generated by emitter 128. The ultrasonic signal, represented by the arrow 129 is reflected by the air flow and the minute particles that carried along 130 to reach the ultrasonic receiver 134. The moving air and suspended particles change in the received sound relative to the emitted sound in the form of a Doppler frequency shift that is detected by the processor 132 powered by the battery 136. The processor 132 also generates the oscillations needed to create the ultrasonic signal and may also contain an integrated microphone for detection of the cough sounds.

Figure 5:
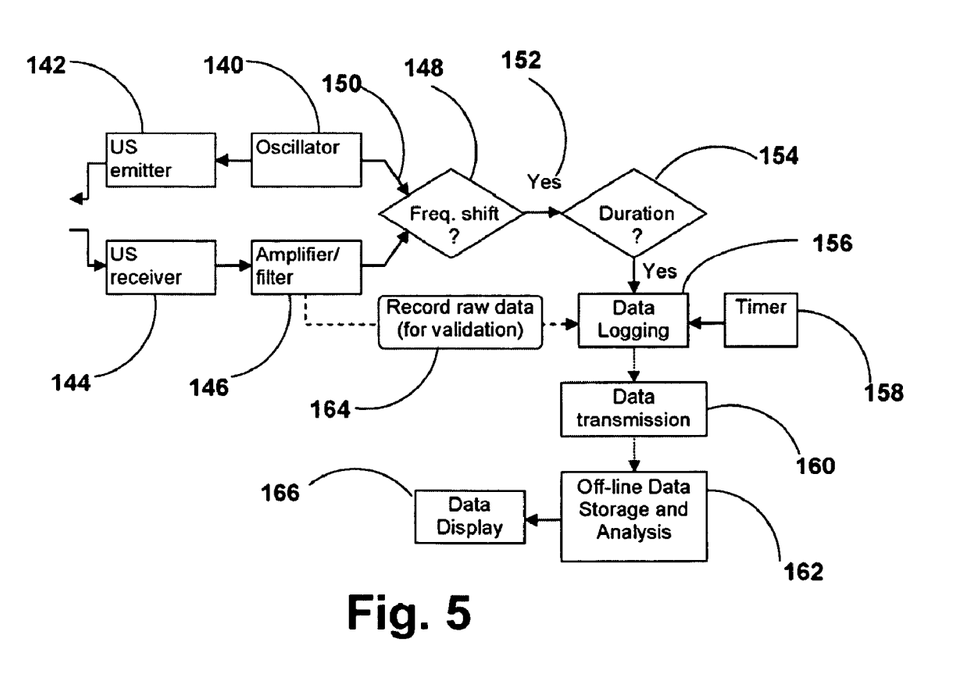
FIG. 5 is a block diagram of the detection method of the ultrasonic cough detector.

The operation of the ultrasonic CD is described in the block diagram shown in FIG. 5 to which reference is now made. Oscillator 140 generates an ultrasound frequency energy that drives the ultrasonic emitter 142. The returning signal is picked up by the ultrasonic receiver 144 and amplified by the amplifier 146. The frequency shift detector 148 receives the signals from the amplifier 146 and through a secondary channel 150 the signal from the oscillator 140. The frequency shift detector 148 determines if there was a frequency shift and if this frequency shift exceeded a threshold. If the threshold was exceeded as indicated by the yes over the arrow 152, a signal is transmitted from the frequency shift detector 148 to the duration detector 154. In an alternative embodiment, the coincidence between the signal indicating that the frequency shift threshold was exceeded and the high frequency signal from the microphone built into the sensor (not shown) is evaluated. Only if there is a coincidence between the timing of both signals the duration detector 154 receives a signal. The duration detector 154 determines if the duration of the signal it receives is within the time duration of a cough as described above and if so, generates a signal that triggers the data logging element 156 to register the event as the presence of a cough. In addition, the time of the event, determined by the timer 158 is recorded in the data logger. Optionally, the raw data from the preceding time period of 2-3 seconds, transiently stored in the raw data recorder 164 may be recorded in the data logger 156 for subsequent analysis or validation. The data stored in the data logger 156 may be transmitted via a transmission element 160 to a permanent storage and analysis element 162 via wire or wireless transmission as a digital or an analog signal. The data from the analyzer 162 may be displayed in graphic or numeric form by the data display element 166.

Data from actual coughs from a patient are shown in FIG. 6A to which reference is now made. The top tracing 180 and the bottom tracing 182 are both plots of amplitude vs. time. The top tracing 180 is the low frequency component of the piezoelectric signal and the bottom tracing 182 is the high frequency component of the piezoelectric signal. The deflection 184 of the low frequency tracing 180 and the oscillation 186 of the high frequency component tracing 182 coincide as indicated by the rectangle 188 that surround both of them. Likewise, the two other rectangles 188 surround events where the low frequency motion of the trachea and the high frequency sound of the trachea coincide, indicating the presence of a cough. The duration of each event is within the time duration of a cough, which confirms that these events are actually coughs.

A wider time frame, which includes the same recording that is shown in FIG. 6A, is shown in FIG. 6B to which reference is now made. The low frequency component 180 and the high frequency component of the piezoelectric sensor are shown. Events in which substantial low frequency tracheal motion 184 coincides with the high frequency loud sounds 186 and represent coughs are shown surrounded by solid rectangles 188. In contrast, events in which there was only high frequency sound are surrounded by broken line rectangles 200 while an event in which only low frequency activity was present is surrounded by a broken line 202. This figure demonstrates the discrimination ability of this new method to differentiate between genuine cough, generated by the index subject and cough-like noises or body motion that are not due to the index subject cough.

Another preferred embodiment of the CD is based on detection of the acute sudden expiratory tracheal flow and deformation generated by coughing through detection of a sudden change in the electrical resistance of the neck. A plurality of electrodes are attached to the neck and transmit an alternating minute current in the range of 5-50 kHz. At least two electrodes are placed adjacent to the sides of the trachea with additional optional electrode used as reference and placed elsewhere around the circumference of the neck. The voltage to current relationship, usually defined as the electrical impedance is continuously tracked. When the person coughs, a sudden change in the tracheal dimensions causes an abrupt transient change in the electrical impedance. This is a direct measure of the motion, which when combined with the sound detected by a microphone or a contact sensor is used to positively identify coughs in the same scheme outlined for the previous two examples described above.

It is clear that any combination of low and high frequency signals may be used.

The invention claimed is:

1. A cough detector adapted to be fit against the neck of a person for detecting and counting coughing events, comprising:
    a single contact sensor capable of simultaneously sensing and transducing both low frequency and high frequency mechanical vibrations, wherein the sensor is configured to be positioned and brought into contact over a lower segment of a cervical trachea of the person;
    a low pass filter for receiving electrical signals from the sensor and selectively passing low frequency signals within a frequency range of 0.5 Hz to 10 Hz;
    a low frequency threshold detector for applying an adaptive or fixed threshold to the low frequency signals;
    a high pass filter for receiving electrical signals from the sensor and selectively passing high frequency signals within a frequency range of 200 Hz to 2000 Hz;
    a high frequency threshold detector for applying an adaptive or fixed threshold to the high frequency signals;
    a coincidence detector for receiving signals from both the low frequency threshold detector and the high frequency threshold detector, wherein the coincidence detector identifies a coincidence between the signals arriving from the low frequency threshold detector and the high frequency threshold detector and generates a continuous signal for the duration of the coincidence;
    a duration detector for determining whether the duration of the continuous signal generated by the coincidence detector is within a range of cough durations, to thereby identify coughing events; and
    a register for storing data concerning coughing events identified as such by the duration detector.

2. The device as in claim 1, wherein the data relating to the coughing events is transmitted to a remote host computer or data logger via a wire or wireless transmitter.

3. The device as in claim 1, wherein the range of cough durations is between 0.1 to 1.5 seconds.

4. A method for detecting and counting coughing events comprising:

a) positioning an ultrasound generator over a lower segment of the cervical trachea of a person;
b) transmitting ultrasonic energy to the cervical trachea by the ultrasound generator;
c) measuring reflected ultrasonic energy from the generated ultrasonic energy through the cervical trachea by an ultrasound receiver, and determining instances of a Doppler frequency shift within the cervical trachea and transmitting Doppler frequency shift signals;
d) positioning a contact sensor or a microphone over the lower segment of the cervical trachea for simultaneously sensing and transducing mechanical vibrations emanating from the cervical trachea segment;
e) filtering the tracheal signal with a high pass filter therein selectively passing high frequency signal within a frequency range of 200 Hz to 2000 Hz;
f) applying a fixed or adaptive high pass threshold to the high pass filtered tracheal signal with a high frequency threshold detector;
g) identifying, by a coincidence detector, coincidence of the Doppler frequency shift signals and the high frequency signal from the high frequency threshold detector;
h) determining, by a duration detector, whether the duration of the coincidence is within a range of cough durations to thereby identify coughing events; and
i) storing, by a register, data concerning coughing events identified as such by the duration detector.

5. A method for automatically detecting and counting coughing events, the method including:
a) positioning a contact sensor over a lower segment of a cervical trachea for simultaneously sensing and transducing tracheal signal emanating from the cervical trachea segment;
b) filtering the tracheal signal with a low pass filter therein selectively passing low frequency portion of the tracheal signal within a frequency range of 0.5 Hz to 10 Hz while simultaneously filtering the tracheal signal with a high pass filter therein selectively passing high frequency signal within a frequency range of 200 Hz to 2000 Hz;
c) applying a fixed or adaptive low pass threshold to the low pass filtered tracheal signal with a low frequency threshold detector;
d) applying a fixed or adaptive high pass threshold to the high pass filtered tracheal signal with a high frequency threshold detector; and
e) identifying a coincidence between a high frequency signal from the high frequency threshold detector and a low frequency signal from the low frequency threshold detector; and
f) determining, by a duration detector, whether the duration of the coincidence is within a range of cough durations to thereby identify coughing events.

6. The method of claim 5 wherein the threshold is a duration based threshold.

7. The method of claim 6 wherein the duration threshold is below 1.5 seconds.

8. The method of claim 5 wherein the coughing event triggers communication with a processor or computer.

9. A cough detector for detecting and counting coughing events, adapted to be fit against the neck of a person, the cough detector comprising:
a) an ultrasound generator for generating ultrasonic energy passed to a cervical trachea through a gel pad disposed about a posterior surface of the cough detector and in contact over a lower segment of the cervical trachea;
b) an ultrasound receiver for measuring reflected ultrasonic energy from the generated ultrasonic energy through the cervical trachea therein determining instances of a Doppler frequency shift within the cervical trachea and transmitting Doppler frequency shift signals;
c) a contact sensor being configured to be positioned and brought into contact over the lower segment of the cervical trachea;
d) a high pass filter for receiving electrical signals from the sensor and selectively passing high frequency signals within a frequency range of 200 Hz to 2000 Hz;
e) a high frequency threshold detector for applying an adaptive or fixed threshold to the high frequency signals;
f) a coincidence detector for receiving the Doppler frequency shift signals and the high frequency signals from the high frequency threshold detector, for identifying coincidence of the Doppler frequency shift signals and the high frequency signals;
g) a duration detector for determining whether the duration of the coincidence is within a range of cough durations, wherein the duration detector identifies coughing events; and
h) a register for storing data concerning coughing events identified as such by the duration detector.

* * * * *